Figure 1:
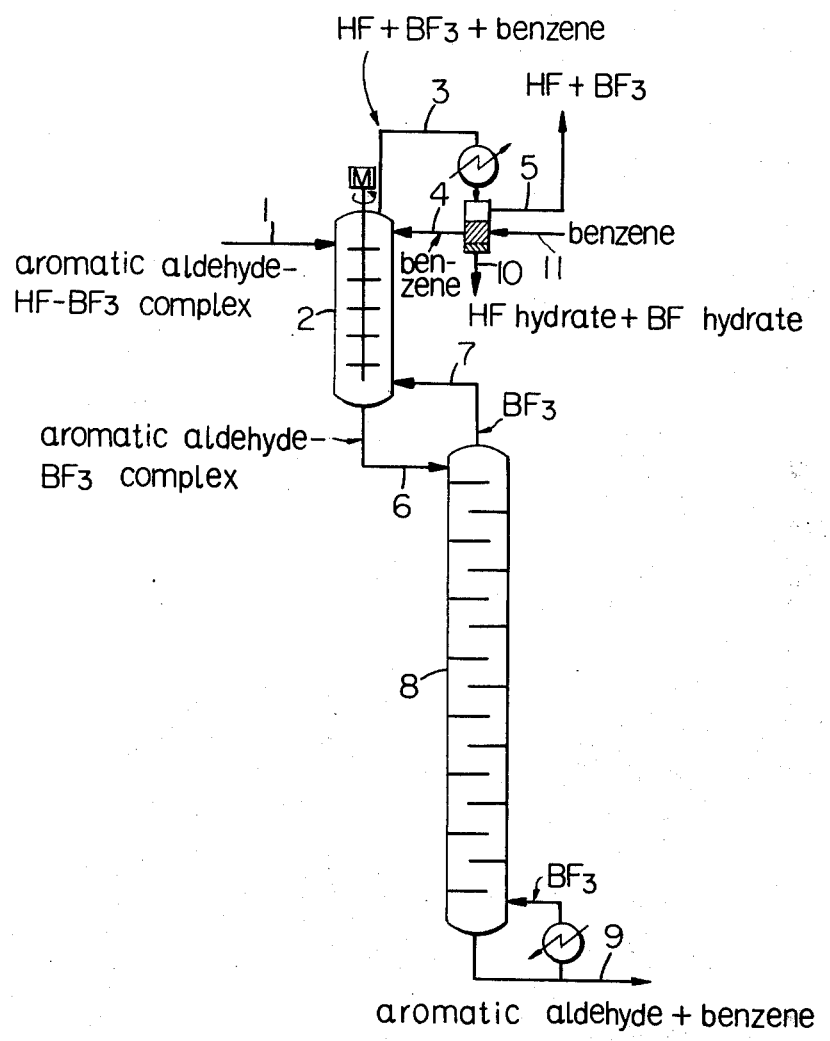

United States Patent [19]
Fujiyama et al.

[11] 3,962,343
[45] June 8, 1976

[54] METHOD FOR DECOMPOSING AN AROMATIC ALDEHYDE-HYDROGEN FLUORIDE-BORON FLUORIDE COMPLEX

[75] Inventors: Susumu Fujiyama; Minoru Takagawa; Shiro Kajiyama, all of Niigata, Japan

[73] Assignee: Mitsubishi Gas Chemical Company, Inc., Tokyo, Japan

[22] Filed: May 8, 1974

[21] Appl. No.: 468,025

[30] Foreign Application Priority Data
May 25, 1973 Japan.............................. 48-58333

[52] U.S. Cl. ............................................ 260/599
[51] Int. Cl.² ...................................... C07C 45/24
[58] Field of Search ................................... 260/599

[56] References Cited
UNITED STATES PATENTS
2,534,017  12/1950  Gresham et al................. 260/599 X

*Primary Examiner*—Bernard Helfin
*Attorney, Agent, or Firm*—Flynn & Frishauf

[57] ABSTRACT

This invention relates to a two-step method for decomposing an aromatic aldehyde-hydrogen fluoride-boron trifluoride complex in the presence of benzene as a diluent to obtain an aromatic aldehyde, hydrogen fluoride and boron trifluoride separately without causing any change in the quality of the aromatic aldehyde or without forming undesirable byproducts.

10 Claims, 1 Drawing Figure

METHOD FOR DECOMPOSING AN AROMATIC ALDEHYDE-HYDROGEN FLUORIDE-BORON FLUORIDE COMPLEX

This invention relates to a method for carrying out heat-decomposition of an aromatic aldehyde-hydrogen fluoride-boron trifluoride complex solution.

A method for reacting an aromatic hydrocarbon with carbon monoxide by using hydrogen fluoride and boron trifluoride as a catalyst to form an aromatic aldehyde is well known. For example, p-tolualdehyde is formed by reacting toluene with carbon monoxide in the presence of a catalyst, and similarly 2,4-dimethyl benzaldehyde and 2,4,5-trimethyl benzaldehyde are formed by reacting m-xylene with carbon monoxide and by reacting pseudocumene with carbon monoxide, respectively.

When the aromatic hydrocarbon reacts with carbon monoxide in the presence of hydrogen fluoride and boron trifluoride as a catalyst, an aromatic aldehyde-hydrogen fluoride-boron trifluoride complex is formed as a reaction product. In carrying out a method for obtaining hydrogen fluoride, boron trifluoride and an aromatic aldehyde separately as products from the complex by decomposing the complex, a change in quality of the aromatic aldehyde is generally prone to occur, so the yield of the aromatic aldehyde is reduced. Furthermore, a small amount of water is dissociated as a result of the reaction causing the change in quality of the aromatic aldehyde. Water so dissociated not only deactivates some of the catalysts, but also corrodes the apparatus used for carrying out the reaction. Therefore, it is necessary to avoid any change in quality of the aromatic aldehyde in case of separating the aromatic aldehyde from the complex, and particularly, the dissociation of water should be kept as low as possible.

It has been difficult to avoid a change in quality of the aromatic aldehyde in case of decomposing the complex according to the prior art. In addition, the recovery ratio for the hydrogen fluoride and boron trifluoride has also been unsatisfactory. For Example, British Patent No. 713,335 discloses a method for continuously obtaining hydrogen fluoride, boron trifluoride and an aromatic aldehyde separately by heat-decomposing an aromatic aldehyde-hydrogen fluoride-boron trifluoride complex, while refluxing a diluent selected the group consisting of toluene and chlorobenzene in the decomposition system. However, the method has the following disadvantages: (a) The undecomposed boron trifluoride in the form of complex remains in the separated aromatic aldehyde, and (b) expensive silver should be used as a material for the reaction vessel to prevent corrosion of the vessel by the water which is dissociated as a result of the reaction causing the change in quality of the aromatic aldehyde. Particularly though, it is commercially preferable that such decomposition be conducted under a superpressure, a striking change in quality of the aromatic aldehyde is anticipated by maintaining the aromatic aldehyde under a superpressure. Therefore, the method of the British Patent which does not eliminate these disadvantages can not be a said to be suitable one. This invention eliminates these disadvantages.

Therefore, it is an object of this invention to provide a commercially usable process for continuously obtaining the aromatic aldehyde, hydrogen fluoride and boron trifluoride separately in a high yield or in a high recovery ratio by decomposing the aromatic aldehyde-hydrogen fluoride-boron trifluoride complex under a superpressure.

Another object of this invention is to provide a process for obtaining an aromatic aldehyde, hydrogen fluoride and boron trifluoride separately without causing any change in the quality of the aromatic aldehyde.

Other objects of the invention will in part be obvious and will in part appear hereinafter.

We, the inventors, have found that the reaction causing the change in quality of the aromatic aldehyde is mainly effected when the aromatic aldehyde is heated in the presence of hydrogen fluoride, and that boron trifluoride contributes little to the reaction of causing the change in quality of the aromatic aldehyde in comparison with hydrogen fluoride. We have also found that the reaction causing the change in quality of the aromatic aldehyde is probably the condensation reaction of an aromatic aldehyde with an aromatic hydrocarbon to form triarylmethane, and that when benzene is added to the decomposition system, the condensation reaction does not take place.

This invention is formed on the basis of this discovery. This invention comprises a method for decomposing an aromatic aldehyde-hydrogen fluoride-boron trifluoride complex in the presence of benzene as a diluent.

This invention also comprises a two-step method for decomposing an aldehyde-hydrogen fluoride-boron trifluoride complex. The first step consists of removing hydrogen fluoride from the complex by rapidly heat-decomposing the complex in the presence of benzene as a diluent and the second step consists of removing boron trifluoride from the aromatic aldehyde-boron trifluoride complex formed by the first step by heat-decomposing this complex under such severe conditions that the aromatic aldehyde-boron trifluoride complex is completely decomposed by using a gasliquid contacting column to obtain the aromatic aldehyde and boron trifluoride separately.

The use of benzene as a diluent in the present invention gives results superior to the use of a methyl-substituted benzene, such as toluene in that it eliminates change in quality of the aromatic aldehyde and the formation of water resulting from the reaction causing such change.

When the aromatic aldehyde-hydrogen fluoride-boron trifluoride complex is heated, hydrogen fluoride is more easily dissociated from the complex to form an aromatic aldehyde-boron trifluoride than boron trifluoride is. The aromatic aldehyde-boron trifluoride complex is a solid material, and can be decomposed only under more severe decomposing conditions than those used in the first step.

However, benzene can dissolve the solid material very well, so a commercially practicable continuous process for decomposing the aromatic aldehyde-boron trifluoride complex is made possible by using benzene as a solvent. Furthermore, the boiling point of benzene is also suitable for decomposing the aromatic aldehyde-hydrogen fluoride-boron trifluoride complex at a pressure of from 1 atm to 10 atms to remove hydrogen fluoride from the complex. When it is required to carry out the decomposition of the complex at a pressure higher than the above pressure, too high a decomposition temperature can be avoided by adding an aliphatic hydrocarbon having a low boiling point, such as pentane or hexane to benzene.

By the term "rapid decomposition" we mean the decomposition which takes place within so short a time as not to cause any change in the quality of the aromatic aldehyde. By "complete decomposition" we mean the decomposition which is effected under such severe conditions that the aromatic aldehyde-boron trifluoride complex is completely decomposed to obtain the aromatic aldehyde and boron trifluoride separately. The degree of decomposition of the complexes is determined by the residence time of the complex in the decomposing columns for the two steps, namely the holdup of the complexes, the form of each of the columns, the length of each of the columns, the heat supplied to each column, the temperature and the pressure in each of the columns, and the kinds of the diluent employed, etc. The decomposing conditions in each of the two steps are decided by taking into account all these factors.

The diluent of this invention acts as a heat transfer medium in the decomposition system of the first step by which hydrogen fluoride is removed from the aromatic aldehyde-hydrogen fluoride-boron trifluoride complex while it is refluxed in the system. The amount of benzene diluent to be supplied must be more than is required only for supplying the heat to the decomposition system. The benzene is refluxed to the top of column and, in general, at least 15 mol, preferably 20 – 30 mol of benzene is required per 1 mol of the aromatic aldehyde introduced to the decomposing column for rapid decomposition. When there is a large amount of benzene vapor existing in the decomposition system, the decomposition of the complexes can be carried out rapidly and completely, because of the lowering of the partial pressure of hydrogen fluoride and boron trifluoride. The upper limit of the amount of benzene employed is decided from the view point of heat economy.

Some of the benzene diluent is removed as a raffinate together with the decomposed aldehyde and some is entrained with a hydrogen fluoride vapor and a boron trifluoride vapor from the decomposition system, so supply of fresh benzene to the decomposing system is constantly required to compensate for the loss of benzene diluent.

As mentioned above, the decomposition of the aromatic aldehyde-hydrogen fluoride-boron trifluoride complex according to the present invention is carried out in two steps. The first step comprises removing hydrogen fluoride from the above complex by rapidly decomposing the complex, and the second step comprises removing boron trifluoride from the aromatic aldehyde-boron trifluoride complex by completely decomposing the complex.

In the first step of this invention, hydrogen fluoride which is prone to cause a change in the quality of the aromatic aldehyde should be removed from the aromatic aldehyde-hydrogen fluoride-boron trifluoride complex by rapid decomposition in the presence of benzene. Examples of decomposing columns suitable for carrying out the first step include a rapid gas-liquid contacting column, such as a spray column, a packed column, a column of film-evaporator type, a plate column having a few plates and an empty column. The column employed in the first step should be designed so that the aromatic aldehyde-hydrogen fluoride-boron trifluoride complex solution is held therein for just a short time. Such removal of hydrogen fluoride may be attained by using a column having not more than 2 theoretical plate numbers. Heat can rapidly be supplied to the aromatic aldehyde-hydrogen fluoride-boron trifluoride complex by contact with the benzene vapor which is refluxed in the first step column. Since the bonding between the aromatic aldehyde and hydrogen fluoride is relatively weak, hydrogen fluoride can be readily removed from the complex in a short period of decomposition of the complex.

After hydrogen fluoride is removed, a strongly bonded aromatic aldehyde-boron trifluoride complex is formed. This complex can be decomposed only under such severe decomposing conditions that the complex may completely be decomposed to obtain the aromatic aldehyde and boron trifluoride separately. Fortunately, the reaction causing the change in quality of the aromatic aldehyde is not effected in the absence of hydrogen fluoride. That is, boron trifluoride contributes very little to the reaction causing the change in quality of the aromatic aldehyde. Therefore, the decomposition of the aromatic aldehyde-boron trifluoride complex in the second step can be carried out at an elevated temperature and/or by using a multiplate gas-liquid contacting column to decompose the complex without causing any change in the quality of the aromatic aldehyde. In the practice for carrying out such decomposition, a gas-liquid contacting column having theoretical plate numbers of at least 10 may be used. Theoretical plate number of 10 – 30 is preferred.

In the second step the diluent is not necessarily required in order to avoid the change in quality of the aromatic aldehyde. Since the aromatic aldehyde-boron trifluoride complex is a solid, a solvent is required to dissolve the complex. Benzene accompanied with the complex from the first step may be conventionally used as such solvent as it is. When the boiling point of benzene is too low to carry out the decomposition under certain decomposing conditions, the addition of hydrocarbons having a high boiling point, such as xylenes are preferable. Solvents other than benzene may also be used alone for the second step column.

The process conditions in each of the decomposing columns are: The temperature in the column for the first step is in the range of from about 40°C to about 130°C, preferably from about 80°C to about 110°C. The pressure in the column for first step is in the range of from about 1 atm to about 10 atms. The temperature in the column for the second step is at least 110°C, preferably in the range of from about 130°C to about 180°C. The pressure in the column for the second step is in the range of from about 1 atm to about 10 atms.

FIG. 1 is a flow sheet showing the embodiment of this invention.

FIG. 1 shows a method for producing p-tolualdehyde by decomposing a p-tolualdehyde-hydrogen fluoride-boron trifluoride complex. A synthetic solution of the p-tolualdehyde-hydrogen fluoride-boron trifluoride complex obtained by reacting toluene with carbon monoxide in the presence of hydrogen fluoride and boron trifluoride as a catalyst is introduced to decomposing column 2 for the first step through line 1. Column 2 is maintained at a pressure of 6 atms. Benzene is refluxed in column 2 as a diluent. The synthetic solution is a p-tolualdehyde-hydrogen fluoride-boron trifluoride complex solution. Column 2 is a distilling column of film-evaporator type so that hydrogen fluoride may be removed from the synthetic solution within a short time. When the complex contacts the benzene vapor in column 2, the complex is decomposed to dissociate hydrogen fluoride from the complex. Hydrogen fluoride, boron trifluoride (which was decomposed in column 8 for the second step and was introduced from column 8 through line 7) and excess benzene vapor are withdrawn from the top of column 2 through line 3, and are introduced to partial condenser 5, in which the vapor is cooled to the temperature at which the benzene is condensed. The benzene so condensed is refluxed to column 2 through line 4. Hydrogen fluoride and boron trifluoride are recovered through line 5, are condensed by cooling, and then are recycled to the reaction system for synthesis of p-tolualdehyde through a suitable means (not shown) for reuse as a catalyst for the synthesis. The catalyst which was deactivated by a very small amount of water is drained off through line 10. The deactivated catalyst is a mixture of a hydrogen fluoride hydrate and a boron trifluoride hydrate. These hydrates are regenerated by any of a variety of well known means to hydrogen fluoride and boron trifluoride anhydride which are reused as a catalyst for synthesis of p-tolualdehyde.

The p-tolualdehyde-boron trifluoride complex which is dissolved in benzene flows down column 8 for the second step through line 6. Column 8 is a distilling column of tray structure having about 20 contacting plates. In column 8, boron trifluoride is completely dissociated from the complex, while the complex solution in benzene falls down. Boron trifluoride so dissociated is fed into the bottom of column 2 through line 7. An about 30% by weight solution of p-tolualdehyde in benzene is drained off from column 8 through line 9. After the very small amount of boron trifluoride contained therein is removed from the solution of p-tolualdehyde by washing with water, the solution is fed into a distilling column (not shown) where the benzene and a very small amount of components having a high boiling point, such as toluene, are removed from p-tolualdehyde. Fresh benzene is fed into partial condenser through line 11 to compensate for the amount of benzene lost through line 9.

In another embodiment of this invention, the two steps may be carried out in the same column. For example, benzene is refluxed in the upper portion of the column, whereas the xylene is refluxed in the lower portion thereof. The first step is carried out in the portion in which benzene is refluxed, whereas the second step is carried out in the portion in which the xylene is refluxed.

The process of this invention has been attained by making the mechanism of the change in quality of the aromatic aldehyde clear. According to this invention, hydrogen fluoride, boron trifluoride and the aromatic aldehyde can be obtained separately from the aromatic aldehyde-hydrogen fluoride-boron trifluoride complex in a high yield by decomposing the complex in the presence of benzene. This invention has the following advantages: (a) The change in quality of aromatic aldehyde, that is the formation of byproduct is very low, even when the decomposition is effected under a superpressure; (b) hydrogen fluoride, boron trifluoride and the aromatic aldehyde are each obtained with the least loss of their amounts; and (c) the columns for carrying out the present process do not have to be made from an expensive corrosion-resistant material, e.g. silver. The present process is commercially usable, so the significance of this invention for industry is great.

The invention is further illustrated, but in no way limited, by the following Examples.

EXAMPLES 1 – 5

A packed column having the inside diameter of 20 mm and the length of 800 mm, filled with McMahon packing of 6 mm was used. A reflux condenser was positioned above the top of the column. Benzene was refluxed in the upper portion within a distance of 200 mm from the top, and m-xylene or p-xylene was refluxed in the under portion below a distance of 200 mm from the top thereof. This was confirmed from the temperature distribution in the column. The pressure employed in the column was 1 atm. The synthetic solution was introduced within a distance of 200 mm from the top. The synthetic solution to be decomposed was p-tolualdehyde, 2,4-dimethylbenzaldehyde or 2,4,5-trimethylbenzaldehyde synthesized from toluene, m-xylene or pseudocumene in the presence of hydrogen fluoride and boron trifluoride as a catalyst, respectively. The catalysts were recovered from the top of the column in a gasous state, whereas the aromatic aldehyde was recovered from the bottom thereof in a state of solution in the xylene. The results of decomposition are given in Table 1. The catalysts which were not recovered in a gasous state from the top of the column were drained off from the bottom of a partial condenser positioned below the reflux condenser as hydrates.

Table 1

| | object product | Example 1 p-tolu- aldehyde | Example 2 p-tolu- aldehyde | Example 3 2,4-dimethyl- benzaldehyde | Example 4 2,4,5-trimethyl- benzaldehyde | Example 5 2,4,5-trimethyl- benzaldehyde |
|---|---|---|---|---|---|---|
| contents of synthetic solution | amount of HF supplied (g/H) | 50.6 | 52.5 | 34.7 | 24.2 | 47.4 |
| | amount of $BF_3$ supplied (g/H) | 39.4 | 26.0 | 27.5 | 19.9 | 36.4 |
| | amount of aromatic aldehyde supplied (g/H) | 54.7 | 38.3 | 43.2 | 35.0 | 65.4 |
| | amount of hydrocarbon supplied *(g/H) | 18.6 | 11.8 | 9.2 | 7.1 | 8.4 |
| diluent | | benzene- m-xylene | benzene- p-xylene | benzene- m-xylene | benzene- m-xylene | benzene- m-xylene |
| amount of vapor in the column (g/H) | | 740 | 730 | 685 | 780 | 650 |
| gas withdrawn from the top of the column | recovery ratio of HF (%) | 99.1 | 98.9 | 98.5 | 99.5 | 99.0 |
| | recovery ratio of $BF_3$ (%) | 98.7 | 98.8 | 98.2 | 99.2 | 98.0 |
| raffinate | recovery ratio of aromatic aldehyde (%) | 98.1 | 98.0 | 98.7 | 99.4 | 99.1 |

Table 1-continued

| object product | Example 1 p-tolu-aldehyde | Example 2 p-tolu-aldehyde | Example 3 2,4-dimethyl-benzaldehyde | Example 4 2,4,5-trimethyl-benzaldehyde | Example 5 2,4,5-trimethyl-benzaldehyde |
| --- | --- | --- | --- | --- | --- |
| undecomposed $BF_3$** | 0.15 | 0.40 | 0.80 | 0.31 | 0.29 |

Note:
*the amount of unreacted hydrocarbon contained in the synthetic solution
**the proportion of undecomposed $BF_3$ to (%) supplied

EXAMPLES 6 AND 7 AND COMPARATIVE EXAMPLES 1 AND 2

The decomposing column for the first step (hereinunder referred to as the first column) is composed of a column of film-evaporator type having a length of 210 mm and a inside diameter of 28 mm, equipped with rotary vanes having the width of 26 mm and the length of 210 mm. The vanes rotate at a rate of 750 r.p.m. The complex solution is decomposed while it flows down through the gap between the inside wall and the side edges of the vanes. There is an inlet for the synthetic solution within a distance of 80 mm from the top of the column.

recovered from the condenser. The liquid stored in the vessel was maintained at a constant level, and the decomposed p-tolualdehyde was continuously withdrawn from the vessel as an about 30% by weight solution of p-tolualdehyde in benzene. Thereafter, any low boiling point fraction, such as benzene and any high boiling point fraction, such as byproducts derived from the aldehyde were successively cut from the solution. The decomposing results are given in Table 2. The unrecovered catalysts in a form of hydrate were drained off from the condenser.

For comparison, the above processes were repeated except that toluene was used as a diluent. The results are given in Table 2 as Comparative Examples.

Table 2

| | | Example 6 | Example 7 | Comparative Example 1 | Comparative Example 2 |
| --- | --- | --- | --- | --- | --- |
| contents of synthetic solution | amount of HF supplied (g/H) | 114.4 | 175.2 | 110.2 | 134.2 |
| | amount of $BF_3$ supplied (g/H) | 70.5 | 127.5 | 78.8 | 90.2 |
| | amount of aromatic aldehyde supplied (g/H) | 86.5 | 140.5 | 88.3 | 100.9 |
| | amount of hydrocarbon supplied *(g/H) | 31.3 | 36.8 | 29.4 | 28.5 |
| diluent | | benzene | benzene | toluene | toluene |
| amount of vapor in the column (g/H) | | 3033 | 3194 | 2970 | 3210 |
| gas withdrawn from the top of the column | recovery ratio of HF (%) | 98.8 | 98.8 | 96.8 | 96.5 |
| | recovery ratio of $BF_3$ (%) | 98.5 | 98.8 | 96.9 | 96.4 |
| raffinate | recovery ratio of p-tolualdehyde | 97.6 | 97.3 | 90.8 | 92.9 |
| | formation ratio of triarylmethane contained in the fraction of high boiling point (%) | 0.23 | 0.21 | 2.5 | 3.2 |
| | undecomposed $BF_3$** (%) | trace | 0.02 | 0.08 | 0.15 |

Note:
*the same as those of Table 1
**the same as those of Table 1

The column for the second step (hereinunder referred to as the second column) is composed of a packed column having an inside diameter of 30 mm and a length of 700 mm, and it is filled with a Dixon packing of 3 mm. A condenser is positioned above the top of the first column for condensation and refluxing of an excess amount of a diluent vapor. The condenser was cooled with water at a temperature of 80°C so as to condense the benzene vapor, but not the hydrogen fluoride. The benzene which was condensed contained a very small of a hydrogen fluoride hydrate and a boron trifluoride hydrate, so a specific contrivance was required to separate these hydrates from benzene as a heavy fluid. A vessel having the inside capacity of 130 ml was arranged below the bottom of the second column. Necessary heat was supplied to the vessel by an electric heater, whereby a benzene vapor was supplied to the second column. Throughout the operation, the entire area of the columns was maintained in benzene under a refluxing state. The pressures in the columns were adjusted to 6 atms by controlling the withdrawal of hydrogen fluoride gas and boron fluoride gas to be

What is claimed is:

1. A method for decomposing an aromatic aldehyde-hydrogen fluoride-boron trifluoride complex to obtain the aromatic aldehyde, hydrogen fluoride and boron trifluoride separately, characterized by introducing the complex to a gas-liquid contacting column for rapid decomposition, and thereafter rapidly decomposing the complex therein in the presence of benzene at atmospheric or superatmospheric pressure and at a temperature of from about 40°C. to about 130°C. to dissociate hydrogen fluoride from the complex, thereby forming an aromatic aldehyde-boron trifluoride complex, and introducing the resulting complex to a gas-liquid contacting column for complete decomposition, and thereafter subjecting the complex to complete decomposition at atmospheric or superatmospheric pressure and at a temperature of from about 110°C. to about 180°C., thereby dissociating boron trifluoride from the complex.

2. The method defined in claim 1 wherein the gas-liquid contacting column is a film-evaporator column.

3. The method defined in claim in wherein the rapid decomposition is carried out at a temperature of from about 80°C to about 110°C.

4. The method defined in claim 1 wherein the complete decomposition is carried out at a temperature of from about 130°C to about 180°C.

5. The method defined in claim 1 wherein at least 15 mol of benzene is refluxed to the top of the column for rapid decomposition per 1 mol of the aromatic aldehyde introduced to the column.

6. The method defined in claim 1 wherein the aromatic aldehyde-hydrogen fluoride-boron trifluoride complex is subjected to rapid decomposition within so short a time as not to cause any change in the quality of the aromatic aldehyde.

7. The method defined in claim 1 wherein the complete decomposition is carried out under such severe conditions that the aromatic aldehyde-boron trifluoride complex is completely decomposed to obtain the aromatic aldehyde and boron trifluoride separately.

8. The method defined in claim 1, wherein said aromatic aldehyde-boron trifluoride complex is so decomposed in the presence of benzene.

9. The method defined in claim 1, wherein said aromatic aldehyde-boron trifluoride complex is so decomposed in the presence of a xylene.

10. The method of claim 1 wherein the gas-liquid contacting column is a packed column.

* * * * *